US012527927B2

(12) United States Patent
Cook

(10) Patent No.: US 12,527,927 B2
(45) Date of Patent: Jan. 20, 2026

(54) DEVICE FOR DISPENSING MEDICATION FOR MIGRAINE TREATMENT

(71) Applicant: Olfax, LLC, Asheville, NC (US)

(72) Inventor: Jason Cook, Asheville, NC (US)

( * ) Notice: Subject to any disclaimer, the term of this patent is extended or adjusted under 35 U.S.C. 154(b) by 1228 days.

(21) Appl. No.: 17/344,625

(22) Filed: Jun. 10, 2021

(65) Prior Publication Data

US 2021/0308393 A1 Oct. 7, 2021

Related U.S. Application Data

(63) Continuation-in-part of application No. 16/863,987, filed on Apr. 30, 2020, now Pat. No. 12,263,295, and a continuation-in-part of application No. 16/533,391, filed on Aug. 6, 2019, now abandoned.

(51) Int. Cl.

*A61M 15/08* (2006.01)
*A61M 11/00* (2006.01)
*A61M 15/00* (2006.01)

(52) U.S. Cl.

CPC .......... *A61M 15/08* (2013.01); *A61M 11/007* (2014.02); *A61M 15/0025* (2014.02); *A61M 15/009* (2013.01)

(58) Field of Classification Search

CPC ........... A61M 5/31548; A61M 5/3159–31593; A61M 15/08; A61M 5/1452; A61M 5/1456; A61M 5/14566; A61M 11/06; A61M 15/0028; A61M 2205/073; A61M 2210/0618; A61M 2202/048; A61M 19/00; A61M 11/007; A61M 11/02; A61M 15/0021; A61M 2202/0241; A61M 2205/276

See application file for complete search history.

(56) References Cited

U.S. PATENT DOCUMENTS

| | | | | |
|---|---|---|---|---|
| 2011/0088692 A1* | 4/2011 | Auerbach | ........... | B05B 11/0027 128/203.12 |
| 2018/0256867 A1* | 9/2018 | Levin | .................... | A61M 15/08 |
| 2019/0111448 A1* | 4/2019 | Greiner-Perth | ..... | B05B 11/1059 |

FOREIGN PATENT DOCUMENTS

| | | | | |
|---|---|---|---|---|
| WO | WO-2017191205 A1 * | 11/2017 | ......... | B05B 11/0027 |

OTHER PUBLICATIONS

Nasacort Instruction for Use (https://web.archive.org/web/20170124190539/https://www.nasacort.ca/en/how-to-use; archived Jan. 24, 2017; accessed Aug. 11, 2022 (Year: 2017).*

* cited by examiner

*Primary Examiner* — Elliot S Ruddie

(57) ABSTRACT

The device for dispensing medication for the treatment of pain, such as head or migraine pain, may comprise a medication applicator and an activator. The medication applicator may store a medication and may dispense the medication as an aerosol mist. The medication applicator may be adapted to dispense the medication through a nostril of a user directed at the posterior nasal cavity. The activator may be operable to release the medication in multiple doses. A first dose may be dispensed upon a first activation of an actuation button, and subsequent doses may be dispensed upon additional activations of the actuation button. Each dose may comprise a predetermined volume of the medication. A safety interlock may prevent premature dispensing of the medication. The invention may be adapted for the user to self-administer the medication while the user is positioned in any preferred physical position.

12 Claims, 8 Drawing Sheets

DEVICE FOR DISPENSING MEDICATION FOR MIGRAINE TREATMENT

CROSS-REFERENCE TO RELATED APPLICATION

This application is a continuation-in-part of U.S. application Ser. No. 16/863,987, filed Apr. 30, 2020, which is a continuation-in-part of U.S. application Ser. No. 16/533,391, filed Aug. 6, 2019 and entitled "Drug Delivery System".

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

BACKGROUND

The application of a local anesthetic, such as lidocaine, to portions of the nasal sinus cavity, especially the sphenopalatine ganglion (SPG), can be effective in reducing the pain associated with migraines. This has been historically accomplished through the use of a cotton swab applicator saturated in viscous local anesthetic and applied intranasally while the migraine sufferer lies in a supine position. However, this method requires the assistance or supervision of a trained medical professional.

BRIEF DESCRIPTION OF THE DRAWINGS

Certain illustrative embodiments illustrating organization and method of operation, together with objects and advantages may be best understood by reference to the detailed description that follows taken in conjunction with the accompanying drawings in which.

DETAILED DESCRIPTION

Figure 1:
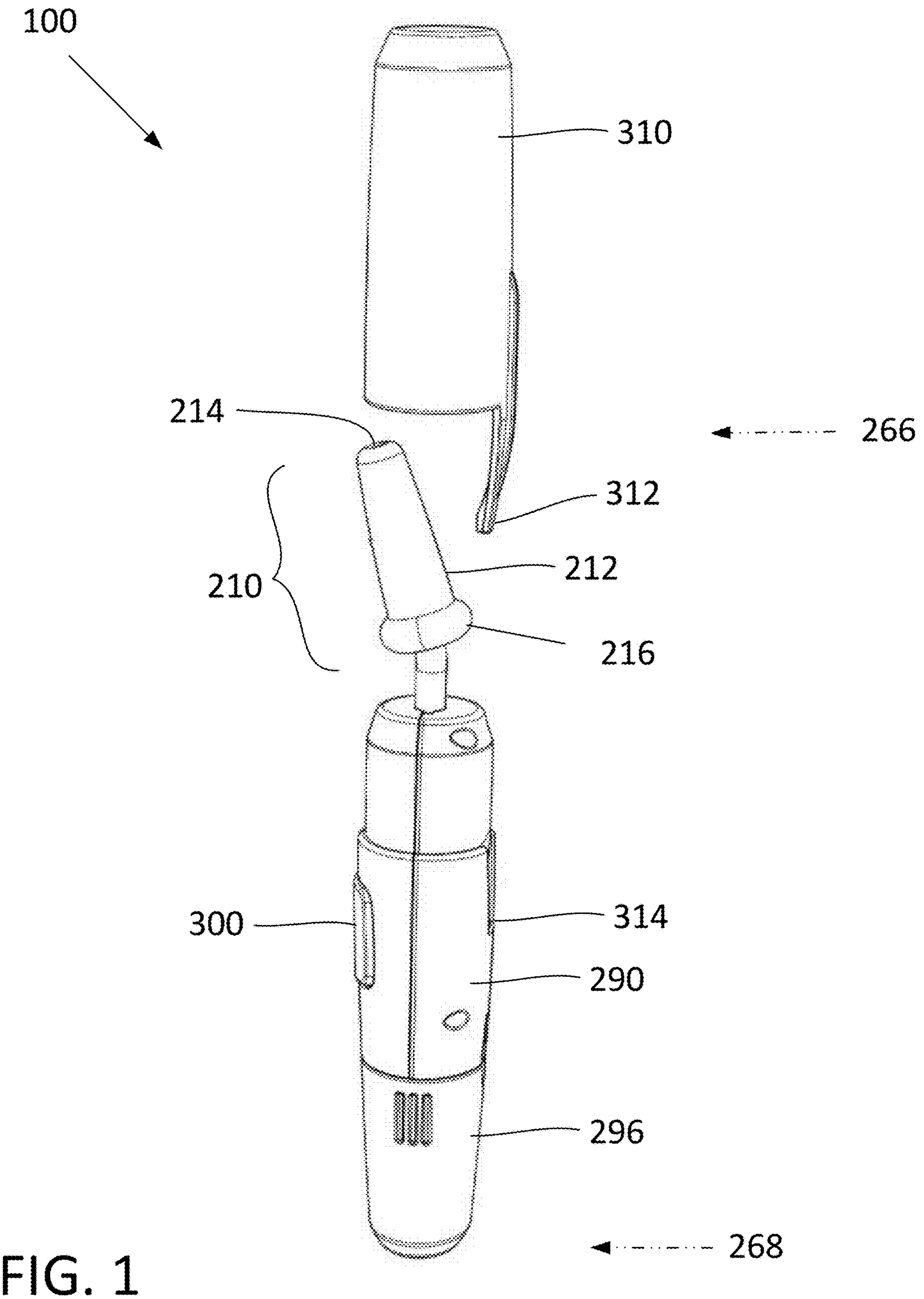
FIG. 1 is an isometric view of the device consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically. The terms 'activation' and 'action of the user', as used herein, may refer to application of the dispensing force to the actuation button.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The device for dispensing medication for pain relief and treatment of conditions that may be effectively treated by the introduction of medications to the sinus cavity may comprise a medication applicator and an activator. In a non-limiting example, a treatment for migraine relief may consist of the introduction of a pain relief medication to the sphenopalatine ganglion (SPG). However, this should in no way be considered the only condition that may be treated through the introduction of medication to the posterior sinus cavity and various physical structures contained therein.

The medication applicator may store a medication and may dispense the medication as an aerosol mist. The medication applicator may be adapted to dispense the medication through an orifice of the user. The orifice may be the first or second nostril of a user directed at a pre-determined position within the posterior nasal cavity. In a non-limiting example, the novel combination product may deliver medication doses to the effective sphenopalatine ganglion (SPG), which efficiently blocks activation of the trigeminovascular system associated with headache disorders and permits the user to self-administer the medication for relief from pain. As noted, additional conditions may be treated through introduction of medication to the posterior nasal cavity through the operation of the medication applicator.

The activator may be operable to release the medication in multiple doses. In a non-limiting example where the applicator is operable to dispense two doses of medication, a first dose may be dispensed upon a first activation of an actuation button and a second dose may be dispensed upon a second activation of the actuation button.

Each dose dispensed by the medication applicator may comprise a predetermined volume of the medication. A safety interlock may prevent premature dispensing of the medication. The invention may be adapted for the user to self-administer the medication. The invention may be adapted to dispense the medication while the user is upright. As non-limiting examples, the user may be sitting, standing, or lying down while using the invention to self-administer a medication, without requiring the assistance of another person.

Throughout this document, proximal refers to a direction that is closer to the user orifice such as, in a non-limiting example, a nostril and distal refers to a direction that is opposite proximal.

The medication applicator may comprise a cartridge, a nozzle, a seal, and a plunger. The medication applicator may dispense the aerosol mist comprising the medication through the nozzle when the plunger pushes the seal towards a proximal end of the cartridge. The nozzle may be designed to deliver medication in a specific pattern and to a specific location as required for the treatment of a particular condition.

The cartridge may be a tubular container for the medication. The cartridge may comprise a nozzle interface, a proximal cartridge aperture, and a distal cartridge aperture. The nozzle interface may be a coupler for accepting the nozzle and may be located on the proximal end of the cartridge. The medication may be forced from within the cartridge through the proximal cartridge aperture which may be located at the center of the nozzle interface. The distal cartridge aperture may be located at a distal end of the cartridge. The seal may slidably interface with the distal cartridge aperture.

In a non-limiting example of medication types to be dispensed, the medication may be a liquid anesthetic. In a preferred embodiment, the medication may be any pre-established formulation or medication. It may be understood, however, that the device may be adapted to dispense numerous medications based upon the fluidity and specification of the medication to be dispensed.

In a non-limiting example, the nozzle may be adapted to direct the medication from the cartridge into the nostril of the user. The nozzle may comprise an atomizer, an insertion limiter, and a cartridge interface. The atomizer may be located at the proximal end of the nozzle and may be configured to dispense medication in particular patterns or quantities necessary to the course of treatment required by the user. The atomizer may convert the medication into the aerosol mist as the medication is forced through one or more apertures under pressure. The pressure may result from proximal movement of the seal within the cartridge during activation. The atomizer may comprise a blunt nasal tip that is to be inserted into the nasal passages to avert nasal trauma to the user. The insertion limiter may be a flange located at the proximal end of the nozzle and axially surrounding the nozzle. The insertion limiter may limit the insertion distance of the nozzle into each nostril. The cartridge interface may mate with the nozzle interface on the cartridge. The medication forced from the cartridge may enter the nozzle via a nozzle aperture in the cartridge interface. The nozzle may bend between the cartridge interface and the atomizer to form an obtuse angle. Additionally, the nozzle may be removed and exchanged for a nozzle with a different angle, nozzle aperture, or configuration that may be suitable for a change in medication or dosage level.

The seal may be a semi-rigid plug that slidably couples to the interior of the cartridge at the distal end of the cartridge. The outer diameter of the seal may match the inner diameter of the cartridge such that the medication is prevent from escaping the cartridge via the distal end of the cartridge. Forward motion of the seal within the cartridge may pressurize the medication and may force the medication out of the cartridge via the proximal cartridge aperture. The seal may be moved proximally in steps such that the medication is dispensed in multiple doses.

The plunger may move the seal in a proximal direction when a dispensing force is applied to the plunger. The plunger may comprise a seal interface at the proximal end of the plunger. The seal interface may mate with the seal such that movement of the plunger is conveyed to the seal. A dispensing spring may be a compression spring. The dispensing spring may apply the dispensing force to the plunger by pressing against the distal end of the plunger. The plunger may be limited by a housing to longitudinal movement within the invention.

The activator may be operable to apply the dispensing force to the plunger such that the plunger may move in a proximal direction to dispense the medication through the nozzle in two or more separate doses. The distance that the plunger moves for each dose may determine the volume of the medication that is dispensed in that dose. The first dose may be dispensed upon the first activation of the actuation button as the plunger moves from a first plunger position to a second plunger position. The first activation may comprise pressing and releasing the actuation button or pressing and holding the actuation button. A subsequent dose of a medication or formulation that has been loaded into the cartridge may be dispensed upon the second activation of the actuation button as the plunger moves from the second plunger position to a third plunger position. In an embodiment, additional doses may be dispensed when the device is configured to dispense multiple doses of a medication or formulation.

The activator may comprise the dispensing spring, the actuation button, a sliding lock, and a lock channel located within the plunger. The actuation button may be a mechanical pushbutton that is accessible through an upper housing. The actuation button may comprise one or more pivot arms that may enable the actuation button to pivot when an actuation force is applied to the actuation button from outside of the upper housing. When pressed inward, the actuation button may convey the actuation force to the sliding lock that is located adjacent to the actuation button such that the sliding lock may slide if the sliding lock is unlocked. The sliding lock may be spring-loaded by one or more lock springs and may apply an opposing force to the actuation button such that the actuation button may move outward to its original position when the actuation force is removed.

The sliding lock may be an armature that is adjacent to the plunger. The sliding lock may be limited by the housing to sliding perpendicularly to the direction of motion of the plunger unless restrained from moving. The sliding lock may be further limited by the housing to sliding in a direction that is oriented towards or away from the actuation button. The sliding lock may comprise a plunger pin which may pass through the lock channel of the plunger and which may prevent proximal motion of the plunger unless features of the lock channel are aligned with the plunger pin.

The lock channel may be a cut-out within the plunger. Proximal movement of the plunger may be limited by mechanical interference between the lock channel and the plunger pin. The features of the lock channel that may control proximal movement of the plunger may be a first offset, a plunger lever, a second offset, and a pin capture channel. The first offset may be a notch located at the proximal end of the lock channel and extending towards the actuation button. The plunger lever may be a semi-rigid hook at a midpoint of the lock channel. The tip of the hook may be pointed towards the actuation button. The plunger lever may be positioned such that a continuous path through the lock channel from proximal end of the lock channel to distal end of the lock channel would exist if not interrupted by the tip of the hook of the plunger lever. The second offset may be a notch located at the midpoint of the lock channel adjacent to the tip of the hook of the plunger lever and extending towards the actuation button. The pin capture channel may comprise the distal end of the lock channel.

Initially, the plunger pin may reside at a first stop position within the first offset and may prevent proximal movement of the plunger. When the actuation force is applied to the actuation button, the sliding lock may be forced to slide and the plunger pin may move out of the first offset. The plunger may then move proximally until the plunger pin is pressed against the plunger lever at a second stop position. The first dose may be dispensed during the proximal movement of the plunger. The actuation button may be released or held without further dispensing of the medication. When the actuation button is released, the one or more lock springs may force the sliding lock to slide such that the plunger pin moves to a third stop position within the second offset. With the plunger pin at the third stop position, proximal motion of the plunger is prevented.

When the actuation force is applied to the actuation button for a second time, the sliding lock may be forced to slide and the plunger pin may move out of the second offset. The plunger pin may press against the top of the hook of the plunger lever and may cause the plunger lever to flex away from the actuation button until the plunger pin aligns with the pin capture channel and the plunger may move proximally. A second dose of the medication stored within the device may be dispensed during the proximal movement of the plunger. Once the plunger pin is within the pin capture channel, the plunger pin may prevent the sliding lock from sliding. The actuation button may remain in the depressed position, indicating that the medication has been completely dispensed and the invention is no longer usable.

The upper housing and a lower housing may comprise the housing that encloses the medication applicator and the activator. A nozzle cap may removably couple to the proximal end of the housing to cover the nozzle. The nozzle cap may comprise a locking extension. When the nozzle cap is in place, the locking extension may penetrate the housing via a locking aperture in the lower housing and may press against the sliding lock such that the sliding lock is prevented from moving. Thus, when the nozzle cap is in place, the actuation button may be prevented from dispensing the medication if pressed unintentionally.

Although the preferred embodiment is described as dispensing two doses, those skilled in the art will recognize that more than two doses may be dispensed by modifications to the invention as described herein. As a non-limiting example, the lock channel may be modified to include additional offsets and plunger levers which define additional stopping positions for the plunger pin.

A first travel distance, defined to be the distance that the plunger travels between the first stop position and the second stop position, may determine the volume of the medication contained in the first dose. A second travel distance, defined to be the distance that the plunger travels between the third stop position and a fourth stop position, may determine the volume of the medication contained in a second dose. In a preferred embodiment, the first travel distance and the second travel distance may be substantially the same such that the first dose and the second dose are the same volume. However, those skilled in the art will recognize that the lock channel may be modified such that the first travel distance and the second travel distance are unequal and therefore a different volume of the medication is dispensed at each activation. Equally, the lock channel may be modified for additional travel distances of either equal or unequal distances to provide different volumes of a medication at each activation for which the device is configured.

In some embodiments, the housing may be configured to allow a spring cap located at the distal end of the housing to be removed for access to the interior of the housing. The spring cap may retain the dispensing spring against the plunger.

In a non-limiting example, for dispensing medication into the nasal passages of a user a first dose may be dispensed with the nozzle inserted into a first nostril and the second dose may be dispensed with the nozzle inserted into a second nostril. As a non-limiting example, the first nostril may be the left nostril and the second nostril may be the right nostril, or vice versa. The capacity of the cartridge may be selected such that both doses may be dispensed into a single nostril without harm. As a non-limiting example, the cartridge may have a capacity of 0.6 ml. The invention may dispense 0.3 ml upon the first activation of the actuation button. The invention may dispense 0.3 ml upon the second activation of the actuation button. Equally, the invention may be configured to deliver different volumes of a medication upon each activation, as well as increasing or decreasing the number of activations that are available to a user in a single cartridge. In a non-limiting example, an alternative dispensing regimen might involve dispensing 0.2 ml on a first actuation of the actuation button and 0.4 ml of a medication on a second actuation of the actuation button.

In use, the invention may be preloaded with the medication. The locking extension on the nozzle cap may prevent the medication from being dispensed if the actuation button is unintentionally pressed. The first dose and the second dose may comprise predetermined dosages of the medication that have been preloaded into the cartridge. The medication may be self-administered by the user once the nozzle cap has been removed. The first dose and the second dose may be individually dispensed by the user via the activator. The medication may be dispensed while the user is in an upright position by placing the nozzle into a nostril and pressing the actuation button to administer the first dose. The actuation button may be pressed and released or pressed, held, and released. The medication may be dispensed into the nostril as an aerosol mist and the aerosol mist may reach the nasal cavity adjacent to the sphenopalatine ganglion. The nozzle may be moved to the other nostril, inserted, and the actuation button pressed a second time to administer the second dose. The actuation button may be left in the depressed position after the second dose as an indication that the invention has been used and no further doses remain.

Turning now to FIG. 1, the figure shows an isometric view of the invention 100 and denotes the proximal end 266 and the distal end 268. The nozzle 210 is shown extending from the housing 290 at the proximal end 266 of the housing 290. The proximal end 266 of the nozzle 210 terminates with the atomizer 212. The atomizer 212 comprises the insertion limiter 216 to limit insertion distance. The atomizer 212 may discharge the medication via the one or more apertures 214. The actuation button 300 is shown accessible on the side of the housing 290. Pressing the actuation button 300 once may dispense the first dose of the medication via the atomizer 212. Pressing the actuation button 300 a second time may dispense a second dose of the medication via the atomizer 212. The nozzle cap 310 is shown separated from the housing 290. The locking extension 312 on the nozzle cap 310 may prevent the actuation button 300 from being pressed when in place on the housing 290 when the locking extension 312 mates with the locking aperture 314. The spring cap 296 may cover the housing 290 at the distal end 268 of the housing 290.

Figure 2:
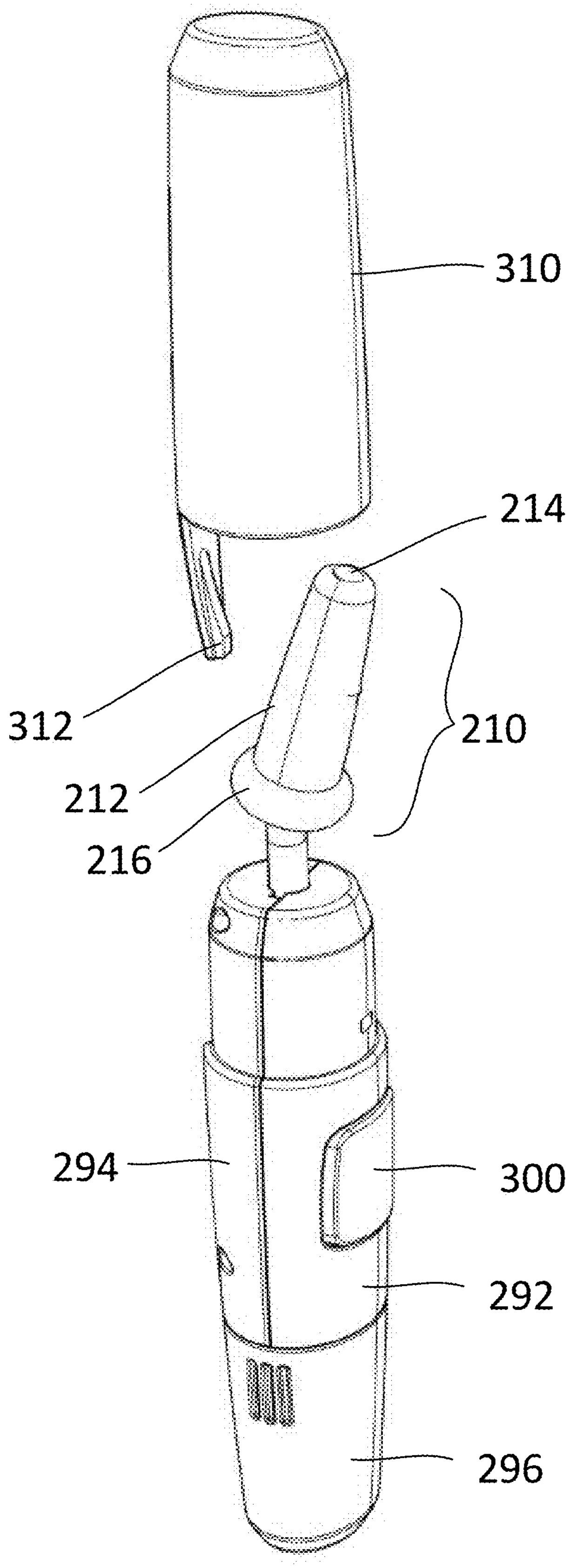
FIG. 2 is a second isometric view of the device consistent with certain embodiments of the present invention.

Turning now to FIG. 2, the figure shows an isometric view from the side opposite that shown in FIG. 1. The nozzle 210 comprising the atomizer 212, the one or more apertures 214, and the insertion limiter 216 is shown. The upper housing 292 and the lower housing 294 are shown with the actuation button 300 accessible on the upper housing 292. The nozzle cap 310 with the locking extension 312 and the spring cap 296 couple to opposite ends of the device.

Figure 3:
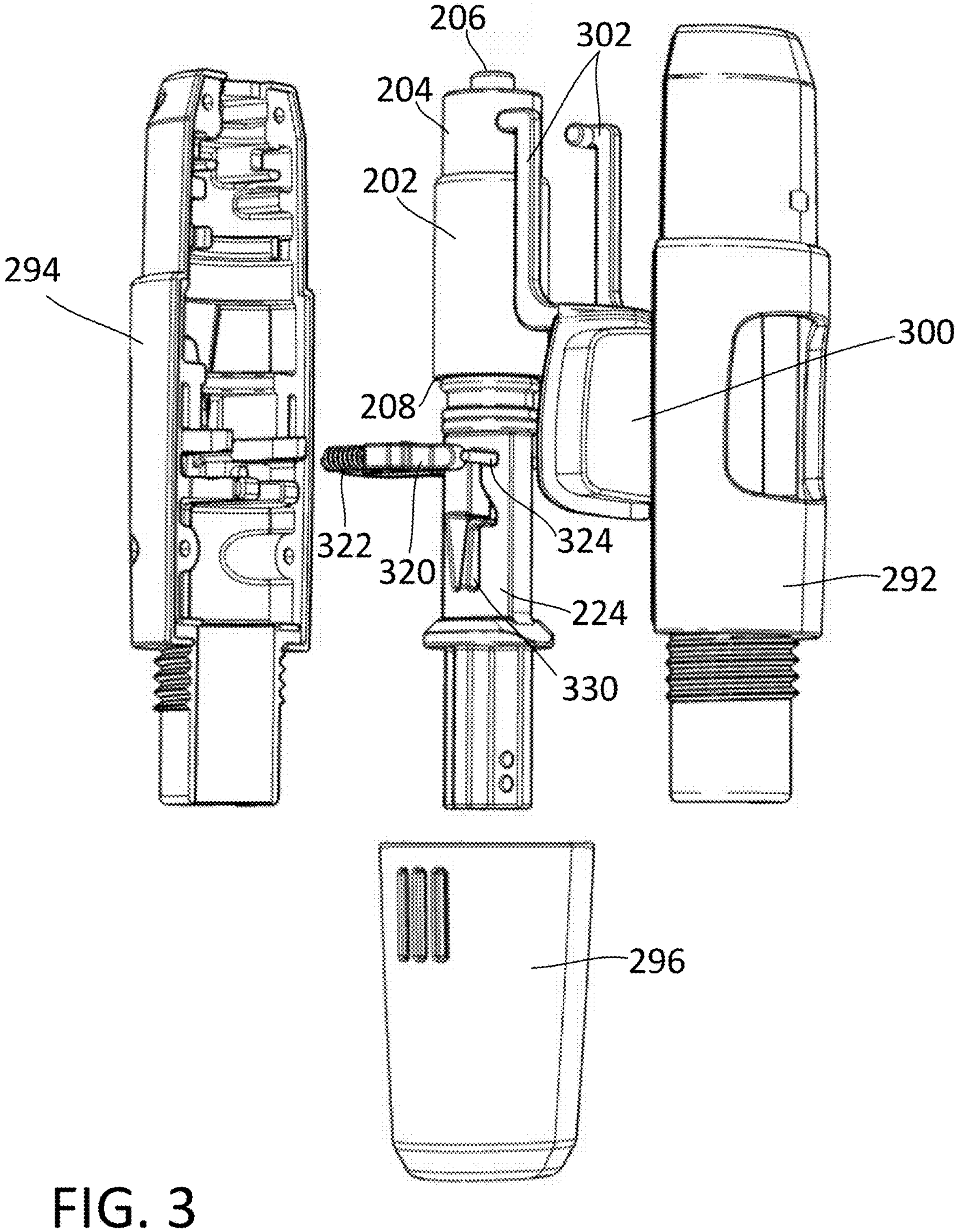
FIG. 3 is an exploded view of the device consistent with certain embodiments of the present invention.

Turning now to FIG. 3, the figure shows an exploded view of the device. Between the upper housing 292 and the lower housing 294 reside the cartridge 202, the plunger 224, the sliding lock 320, and the actuation button 300. The cartridge 202 comprises the nozzle interface 204 that couples to the nozzle 210 and the proximal cartridge aperture 206 through which the medication exits the cartridge 202. The cartridge 202 comprises the distal cartridge aperture 208 which is where the plunger 224 presses in order to force the medication out of the cartridge 202.

The plunger 224 may move proximally (up in this figure) to dispense the medication. The sliding lock 320 may slide laterally under the influence of the actuation button 300 and the one or more lock springs 322. As the sliding lock 320 slides it may reposition the plunger pin 324 within the lock channel 330. The plunger 224 may move if there is no mechanical interference between the plunger pin 324 and the lock channel 330 or may be prevented from moving if there is mechanical interference between the plunger pin 324 and the lock channel 330. The actuation button 300 may comprise the one or more pivot arms 302 allowing the actuation button 300 to pivot when pressed. The spring cap 296 may removably couple to the upper housing 292 and the lower housing 294 via a threaded interface.

Figure 4:
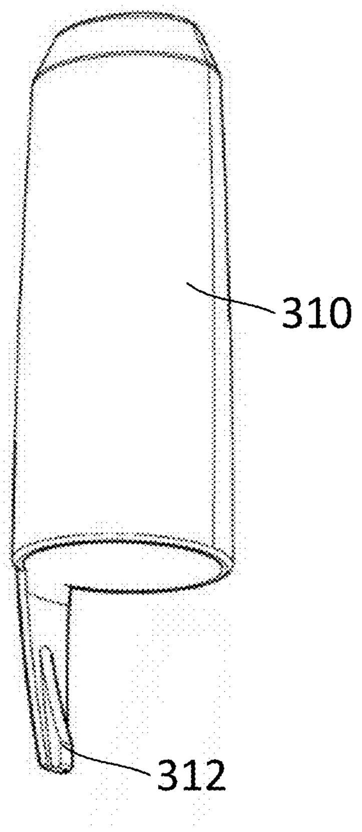
FIG. 4 is a detail view of the device consistent with certain embodiments of the present invention illustrating the nozzle cap.

Turning now to FIG. 4, the figure shows a detail view of the nozzle cap 310 illustrating the locking extension 312.

Figure 5:
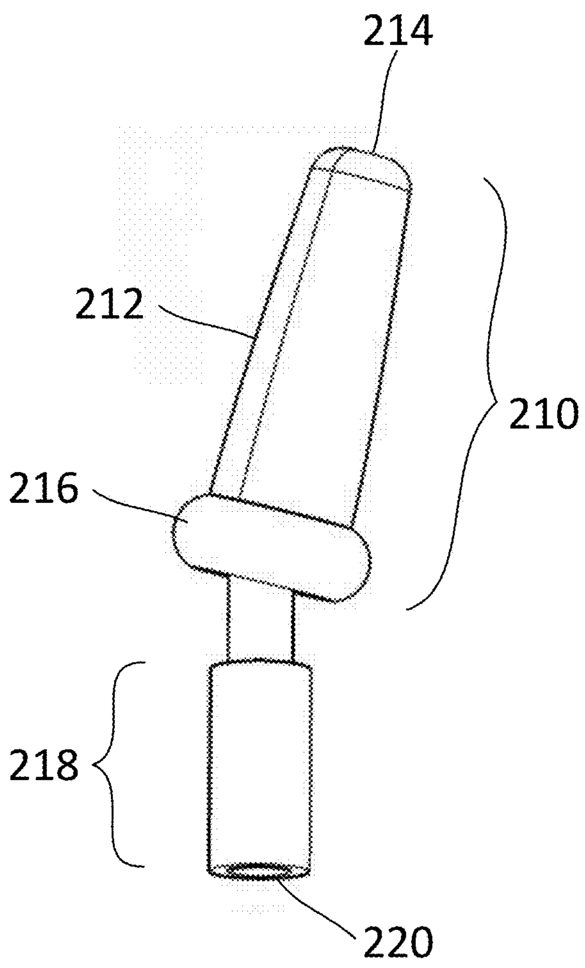
FIG. 5 is a detail view of the device consistent with certain embodiments of the present invention illustrating the nozzle.

Turning now to FIG. 5, the figure shows a detail view of the nozzle 210 illustrating the cartridge interface 218 with the nozzle aperture 220 and the nozzle 210 with the atomizer 212, the one or more apertures 214 and the insertion limiter 216. The medication may be forced into the nozzle aperture 220 and may emerge from the one or more apertures 214 as a mist or other spray pattern as determined by the nozzle orifice and actuation. The nozzle 210 may be placed into a nostril with the insertion limiter 216 preventing over insertion.

Figure 6:
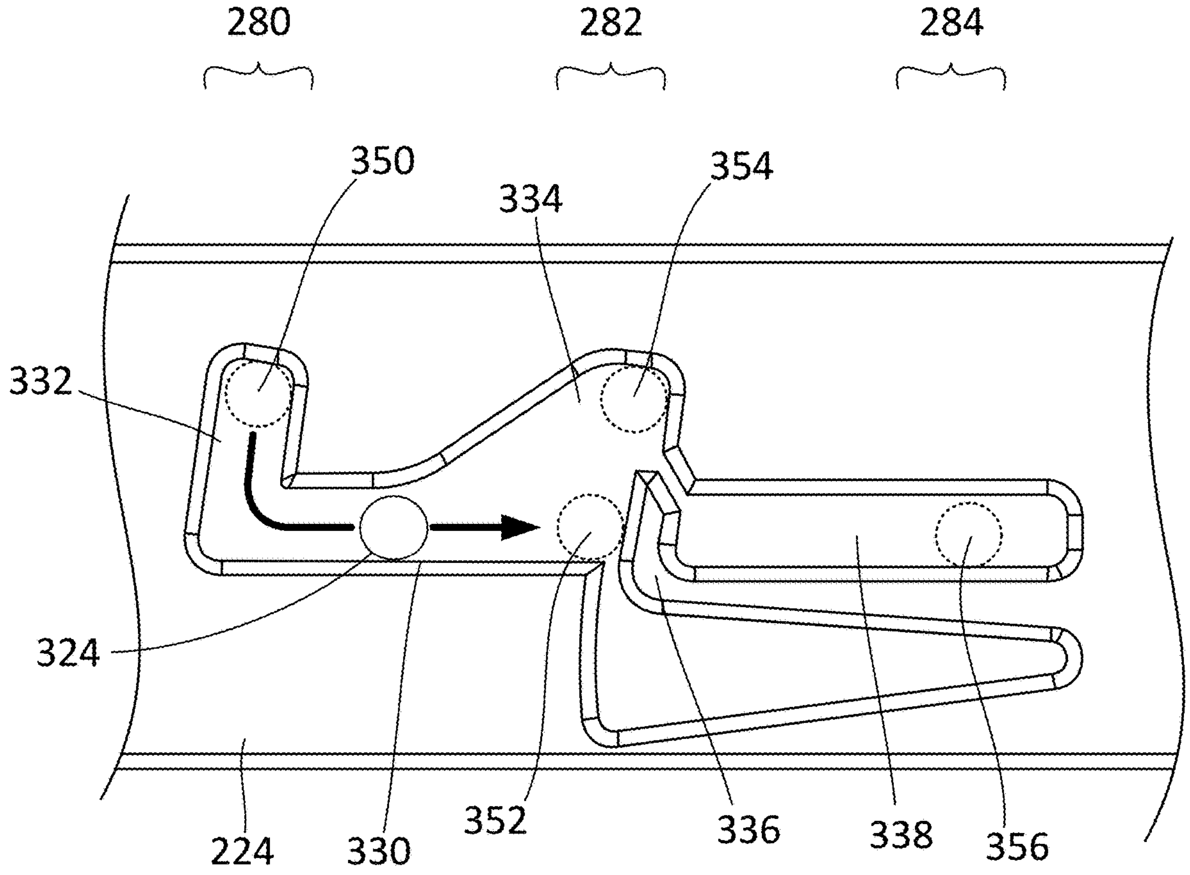
FIG. 6 is a detail view of the device consistent with certain embodiments of the present invention illustrating features of the lock channel.

Turning now to FIG. 6, the figure shows a detail involving the lock channel 330. Note that throughout the description of FIG. 6, the plunger 224 is represented in a stationary position and the plunger pin 324 is represented as moving to the right to various stopping positions. In actuality, the plunger pin 324 is stationed in the horizontal direction and it is the plunger 224 that moves to the left to reposition the plunger pin 324 relative to the plunger 224.

The lock channel 330 may be a cut-out within the plunger 224. The lock channel 330 may comprise the first offset 332, the second offset 334, the plunger lever 336, and the pin capture channel 338. Initially, the plunger 224 will align with the plunger pin 324 at the first plunger position 280. Specifically, the plunger pin 324 will be located at the first stop position 350 within the first offset 332. As the dispensing spring pushes the plunger 224 to the left, the plunger pin 324 at the first stop position 350 may prevent the plunger 224 from moving.

When the actuation button is pressed for a first time, the sliding lock may be pushed down and the plunger pin 324 may drop. The plunger 224 may then be free to slide to the left such that the plunger pin 324 is relocated to a subsequent second stop position 352. Movement of the plunger 224 may be stopped when the plunger pin 324 encounters the plunger lever 336. The actuation button may be held down or released immediately. When the actuation button is released, the one or more lock springs may push the sliding lock up, moving the plunger pin 324 to the third stop position 354. Movement of the plunger 224 may be blocked by the plunger pin 324 when the plunger pin 324 is at the third stop position 354. In moving between the first plunger position 280 and the second plunger position 282, the plunger 224 may have caused the first dose to be dispensed.

When the actuation button is pressed for a second time, the sliding lock may be pushed down and the plunger pin 324 may drop. The plunger 224 may press down on the plunger lever 336, causing the plunger lever 336 to flex downward. When the plunger pin 324 is aligned with the pin capture channel 338, the plunger 224 may move to the left again. As the plunger 224 moves to the left, the plunger pin 324 may enter the pin capture channel 338 and may move to the fourth stop position 356. When the plunger pin 324 is within the pin capture channel 338, the plunger pin 324 may be prevented from moving upwards when the actuation button is released. Having the actuation button stuck in the pressed position is an indication that the device is spent. In moving between the second plunger position 282 and the third plunger position 284, the plunger 224 may have caused the second dose to be dispensed. In an alternative embodiment, additional doses may be configured to be dispensed by the addition of additional plunger positions.

Turning now to FIGS. 7A-D the figure shows details views illustrating movement of the plunger 224.

Figure 7A:
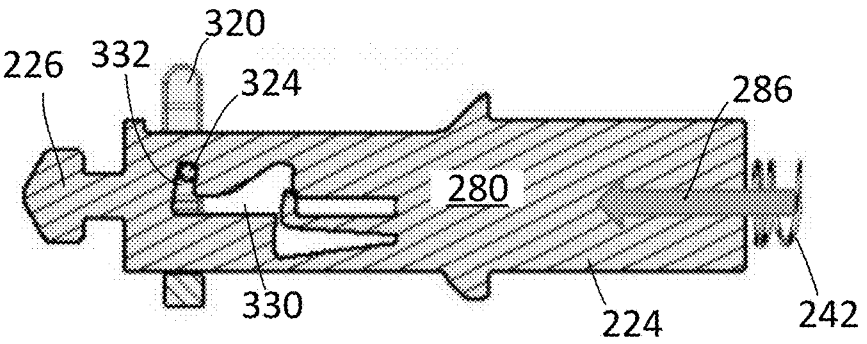
FIG. 7A is a detail view of the device consistent with certain embodiments of the present invention illustrating the plunger in a first plunger position.

FIG. 7A illustrates the plunger 224 in the first plunger position 280. The sliding lock 320 is elevated such that the plunger pin 324 is within the first offset 332 of the lock channel 330. The dispensing spring 242 may apply the dispensing force 286 to the plunger 224 such that the dispensing force 286 tends to push the plunger 224 to the left. Whenever the plunger 224 moves to the left, the seal interface 226 may push the seal into the cartridge. Mechanical interference between the plunger pin 324 and the plunger 224 may prevent the plunger 224 from moving to the left.

Figure 7B:
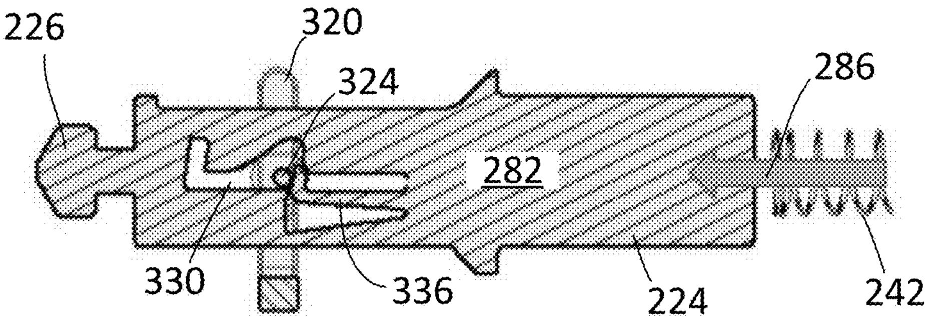
FIG. 7B is a detail view of the device consistent with certain embodiments of the present invention illustrating the plunger in a second plunger position with the sliding lock depressed.

FIG. 7B illustrates the plunger 224 in the second plunger position 282. The dispensing spring 242 may apply the dispensing force 286 to the plunger 224 such that the dispensing force 286 tends to push the plunger 224 to the left. The sliding lock 320 has been forced down by a first depression of the actuation button and has lowered the plunger pin 324. With mechanical interference between the plunger pin 324 and the lock channel 330 eliminated, the plunger 224 may be free to move to the left until the plunger pin 324 contacts the plunger lever 336. In moving between the first plunger position 280 and the second plunger position 282, the plunger 224 may have caused the first dose to be dispensed.

Figure 7C:
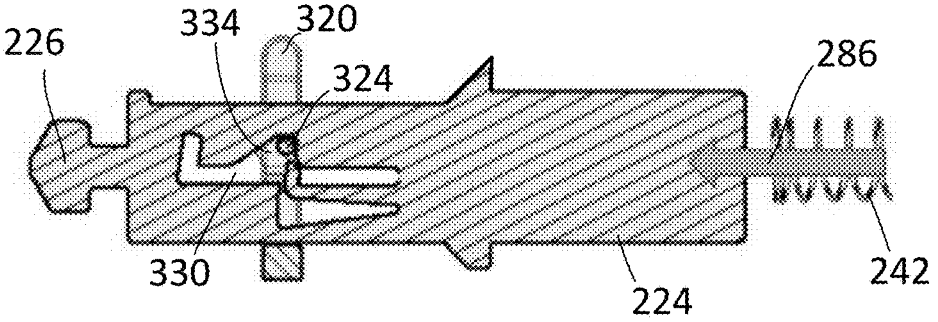
FIG. 7C is a detail view of the device consistent with certain embodiments of the present invention illustrating the plunger in a second plunger position with the sliding lock released.

FIG. 7C illustrates that the actuation button has been released. The dispensing spring 242 may apply the dispensing force 286 to the plunger 224 such that the dispensing force 286 tends to push the plunger 224 to the left. and the one or more lock springs have forced the sliding lock 320 and the plunger pin 324 upwards, positioning the plunger pin 324 within the second offset 334 of the lock channel 330. Mechanical interference between the plunger pin 324 and the lock channel 330 may prevent the plunger 224 from moving to the left.

Figure 7D:
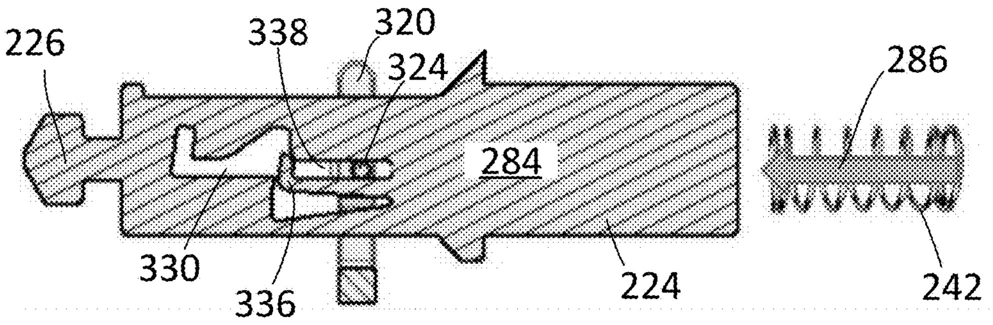
FIG. 7D is a detail view of the device consistent with certain embodiments of the present invention illustrating the plunger in a third plunger position.

FIG. 7D illustrates the plunger 224 in the third plunger position 284. The dispensing spring 242 may apply the dispensing force 286 to the plunger 224 such that the dispensing force 286 tends to push the plunger 224 to the left. The sliding lock 320 has been forced down by a second depression of the actuation button and has lowered the plunger pin 324. As the plunger pin 324 is forced downwards, the plunger pin 324 may press against the top pf the plunger lever 336 and may flex the plunger lever 336 downwards. When the plunger pin 324 is aligned with the pin capture channel 338, the plunger 224 may move to the left to the third plunger position 284. The plunger pin 324 may be vertically trapped within the lock channel 330 at the pin capture channel 338 and may prevent the sliding lock 320 from lifting the actuation button. In moving between the second plunger position 282 and the third plunger position 284, the plunger 224 may have caused the second dose to be dispensed.

Figure 8:
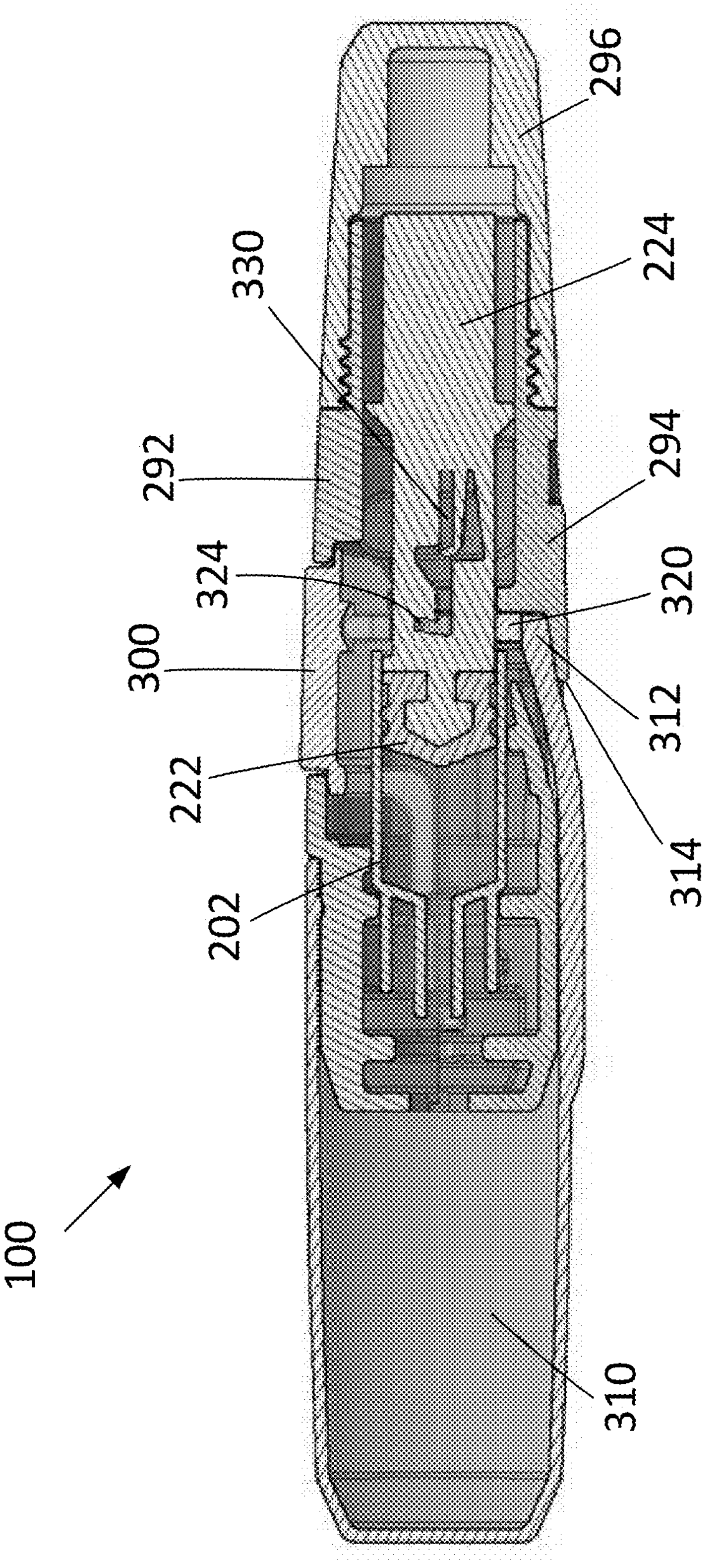
FIG. 8 is a cross-sectional view of the device consistent with certain embodiments of the present invention.

Turning now to FIG. 8, the figure shows a cross-sectional view of the invention 100 in an unused state. The plunger 224 may force the seal 222 into the cartridge 202 to dispense the medication when the actuation button 300 is depressed. The actuation button 300 may be accessible through the upper housing 292. When the actuation button 300 is depressed, the actuation button 300 may force the sliding lock 320 and the plunger pin 324 downwards. When the actuation button 300 is released, the one or more spring locks may force the sliding lock 320 and the plunger pin 324 upwards. The downward and upward movement of the plunger pin 324 may allow the plunger 224 to move forward as the plunger pin 324 moves through the lock channel 330 in stages. The nozzle cap 310 may prevent actuation when the nozzle cap 310 is in place on the housing. Specifically, the locking extension 312 of the nozzle cap 310 may press into the lower housing 294 via the locking aperture 314. The locking extension 312 may cause mechanical interference with the sliding lock 320 and may prevent the sliding lock 320 and the plunger pin 324 from moving downwards.

Figure 9:
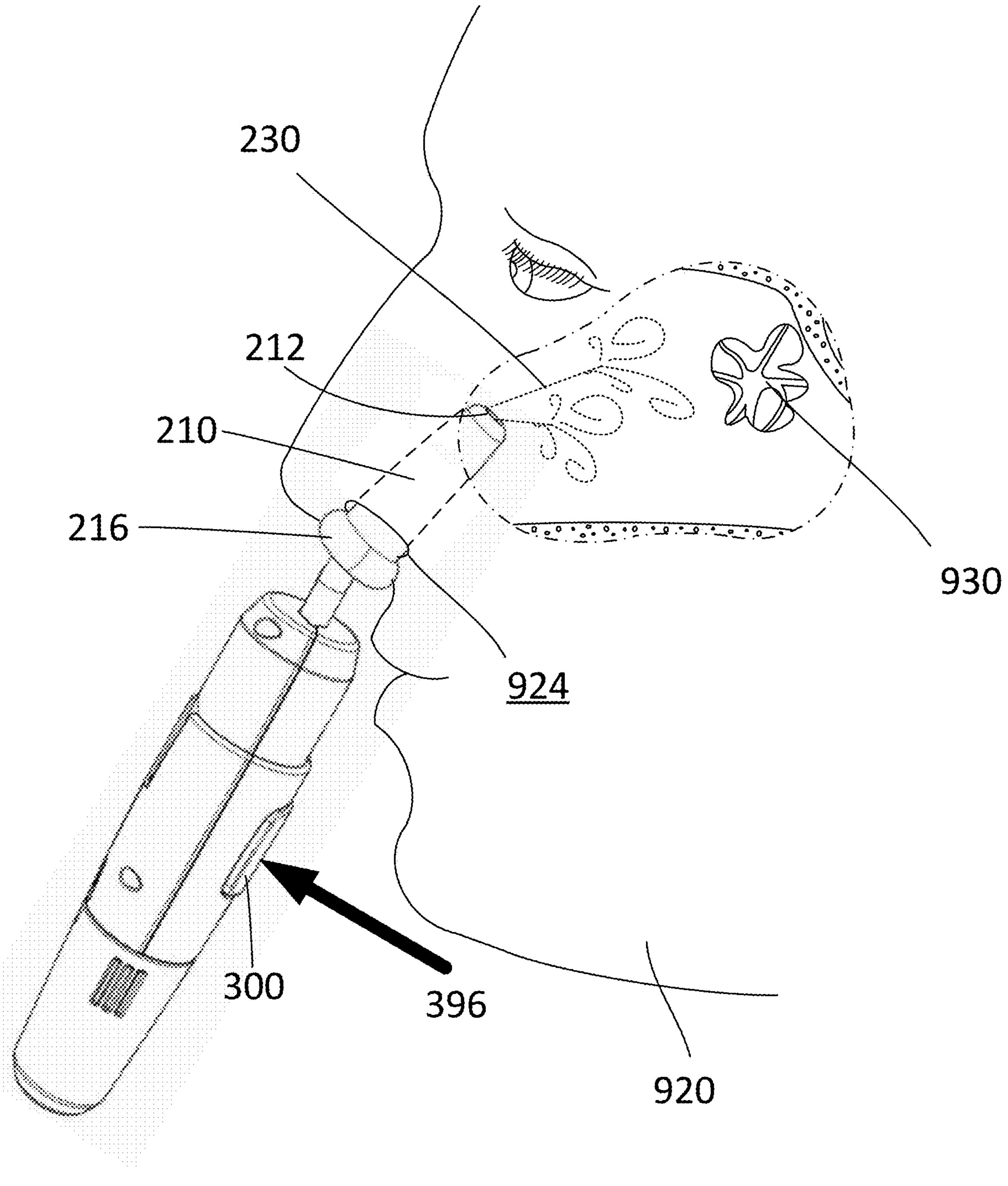
FIG. 9 is an in-use view of the device consistent with certain embodiments of the present invention.

Turning now to FIG. 9, the figure shows the use of an embodiment of the disclosure where the innovation is configured to dispense two doses of a medication by action of the user, although this should in no way be considered as limiting as the innovation may be configured to dispense additional doses of medication when required to treat specific conditions. The user 920 may hold the device with the nozzle 210 inserted into the first nostril such that the insertion limiter 216 of the nozzle 210 is pressed against the nostril 924. Applying the actuation force 396 to the actuation button 300 for a first time may result in the aerosol mist 230 being dispensed via the atomizer 212 into the first nostril. The nozzle 210 may be moved to the second nostril and the dispensing force 286 may be applied to press the actuation button 300 a second time to dispense the aerosol mist 230 into the second nostril. The aerosol mist 230 may travel through the nasal cavities until the medication is adjacent to the sphenopalatine ganglion 930 and may thus provide relief.

While certain illustrative embodiments have been described, it is evident that many alternatives, modifications, permutations and variations will become apparent to those skilled in the art in light of the foregoing description.

What is claimed is:

1. A device for dispensing medication comprising:
a medication applicator and an activator;
where the device dispenses one or more doses of a medication via the medication applicator when activated by said activator;
where the device is adapted for a user to self-administer the medication;
where the activator comprises an actuation button, a sliding lock, a plunger, a plunger pin, a lock channel, and one or more lock springs;
said sliding lock comprising the plunger pin which passes through a lock channel of the plunger to prevent proximal motion of the plunger through action of a lock spring;
where the plunger pin is placed in a first plunger position and the sliding lock is engaged prior to any action of the actuation button and the actuation button is in a non-pressed position: where pressing said actuation button a first time disengages the sliding lock and drops the plunger pin to relocate the plunger pin to a second plunger position and dispenses a dose of medication: relocation of the plunger pin to dispense the dose of medication engages the sliding lock and returns the actuation button to a non-pressed position: where each press of said actuation button disengages the sliding lock and relocates the plunger from the second plunger position to a final plunger position and dispenses an additional dose of medication;
where the plunger pin retains the actuation button in a pressed position when all medication has been dispensed from the medication applicator;
where the medication is dispensed into an orifice as an aerosol.

2. The device according to claim 1
where the medication applicator stores the medication and dispenses the medication as an aerosol mist;
the medication applicator is adapted to dispense the medication where said orifice is a nostril of the user;
where the medication applicator is adapted to direct the medication at a pre-determined location in the posterior nasal cavity.

3. The device according to claim 1
where a nozzle of the medication applicator bends to form an obtuse angle;
where the bend is located between an atomizer at a proximal end of the nozzle and a cartridge of the medication applicator.

4. The device according to claim 3
where the nozzle comprises an insertion limiter;
where the insertion limiter is a flange located proximally on the nozzle and axially surrounding the nozzle;
where the insertion limiter limits the insertion distance of the nozzle into said nostril.

5. The device according to claim 1
where the activator is adapted to dispense the medication responsive to an action of the user;

where the activator comprises a plunger that is moved proximally by one or more of said lock springs;

where the plunger pushes a seal into a cartridge to dispense one dose of the medication.

6. The device according to claim 5 where the action of the user comprises application of a dispensing force to the actuation button.

7. The device according to claim 1 where the activator is operable to release the medication in one or more single doses;

where a first dose is dispensed into a first orifice;

where a second dose is dispensed into a second orifice.

8. The device according to claim 7 where the first dose of the medication is dispensed upon the first activation of the actuation button;

where the second dose of the medication is dispensed upon the second activation of the actuation button.

9. The device according to claim 1 where the device further comprises a safety interlock;

where the safety interlock prevents premature dispensing of the medication.

10. The device according to claim 9 where the safety interlock comprises a locking extension of a nozzle cap;

where the locking extension passes through a housing of the device when the nozzle cap is coupled to the housing.

11. The device according to claim 10 where the actuation button is prevented from moving when the nozzle cap is coupled to the housing or when the medication in the cartridge has been expended;

where the actuation button is permitted to move when the nozzle cap is removed from the housing and at least one dose of the medication remains in the cartridge.

12. The device according to claim 1 where the medication dispensed by the medication applicator is a pre-configured strength and volume.

* * * * *